United States Patent
Delaney, Jr. et al.

(10) Patent No.: US 9,855,415 B2
(45) Date of Patent: Jan. 2, 2018

(54) MEDICAL ELECTRICAL LEAD WITH BIOSTABLE PVDF-BASED MATERIALS

(71) Applicant: Cardiac Pacemakers, Inc., St. Paul, MN (US)

(72) Inventors: Joseph T. Delaney, Jr., Minneapolis, MN (US); David R. Wulfman, Minneapolis, MN (US); Adeniyi O. Aremu, Brooklyn Park, MN (US); Adegbola O. Adenusi, Burnsville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 15/217,178

(22) Filed: Jul. 22, 2016

(65) Prior Publication Data

US 2017/0021160 A1     Jan. 26, 2017

Related U.S. Application Data

(60) Provisional application No. 62/197,000, filed on Jul. 25, 2015.

(51) Int. Cl.
*A61N 1/00* (2006.01)
*A61N 1/05* (2006.01)
*D01D 5/24* (2006.01)

(52) U.S. Cl.
CPC .............. *A61N 1/05* (2013.01); *A61N 1/056* (2013.01); *D01D 5/24* (2013.01)

(58) Field of Classification Search
CPC ............. A61N 1/05; A61N 1/056; D01D 5/24
See application file for complete search history.

(56) References Cited

U.S. PATENT DOCUMENTS

| 5,861,023 | A | 1/1999 | Vachon |
| 7,091,412 | B2 * | 8/2006 | Wang ................ A61M 25/0045 |
| | | | 174/391 |

(Continued)

FOREIGN PATENT DOCUMENTS

| AU | 2012295332 B2 | 12/2014 |
| GB | 1527592 A | 10/1978 |

(Continued)

OTHER PUBLICATIONS

International Search Report and Written Opinion issued in PCT/US2016/043580, dated Oct. 13, 2016, 11 pages.

(Continued)

*Primary Examiner* — George Manuel
(74) *Attorney, Agent, or Firm* — Faegre Baker Daniels, LLP

(57) ABSTRACT

A medical electrical lead includes an insulative lead body extending from a distal region to a proximal region, a conductor disposed within the insulative lead body and extending from the proximal region to the distal region, an electrode disposed on the insulative lead body and in electrical contact with the conductor, and a fibrous matrix disposed on at least part of the electrode. The fibrous matrix includes fibers. The fibers include a polyvinylidene fluoride-based (PVDF-based) polymer and a crystal-modifying additive. The PVDF-based polymer includes an amorphous PVDF phase and a crystalline PVDF phase. The crystalline PVDF phase includes a beta form crystalline structure in an amount exceeding any other crystalline structure form in the crystalline PVDF phase.

18 Claims, 4 Drawing Sheets

(56) References Cited

U.S. PATENT DOCUMENTS

| | | | |
|---|---|---|---|
| 7,689,291 | B2 | 3/2010 | Polkinghorne et al. |
| 7,908,016 | B2 | 3/2011 | Atanasoska et al. |
| 8,903,506 | B2 | 12/2014 | Arnholt et al. |
| 8,965,531 | B2 | 2/2015 | Arnholt et al. |
| 9,415,206 | B2 | 8/2016 | Arnholt et al. |
| 2004/0175406 | A1 | 9/2004 | Schwarz |
| 2005/0149158 | A1 | 7/2005 | Hunter et al. |
| 2006/0264577 | A1 | 11/2006 | Faust et al. |
| 2007/0051531 | A1 | 3/2007 | Borgaonkar et al. |
| 2007/0067882 | A1 | 3/2007 | Atanasoska et al. |
| 2007/0239245 | A1 | 10/2007 | Borgaonkar et al. |
| 2007/0255378 | A1 | 11/2007 | Polkinghorne et al. |
| 2008/0071338 | A1 | 3/2008 | Jiang et al. |
| 2009/0076530 | A1 | 3/2009 | Fukutomi et al. |
| 2009/0099441 | A1 | 4/2009 | Giszter et al. |
| 2009/0099634 | A1 | 4/2009 | Atanasoska et al. |
| 2009/0105796 | A1 | 4/2009 | Atanasoska et al. |
| 2009/0326077 | A1 | 12/2009 | Desai et al. |
| 2010/0023104 | A1 | 1/2010 | Desai et al. |
| 2010/0057197 | A1 | 3/2010 | Weber et al. |
| 2010/0069578 | A1 | 3/2010 | Faust et al. |
| 2010/0179298 | A1 | 7/2010 | Faust et al. |
| 2010/0241204 | A1 | 9/2010 | Scheuermann |
| 2010/0241208 | A1 | 9/2010 | Pinchuk |
| 2011/0021899 | A1 | 1/2011 | Arps et al. |
| 2011/0054580 | A1 | 3/2011 | Desai et al. |
| 2011/0054581 | A1 | 3/2011 | Desai et al. |
| 2011/0137389 | A1 | 6/2011 | Polkinghorne et al. |
| 2011/0196464 | A1 | 8/2011 | Pinchuk |
| 2013/0013040 | A1 | 1/2013 | Desai et al. |
| 2013/0041442 | A1 | 2/2013 | Arnholt et al. |
| 2013/0131765 | A1 | 5/2013 | Polkinghorne et al. |
| 2013/0231733 | A1 | 9/2013 | Knisley et al. |
| 2013/0238086 | A1 | 9/2013 | Ballard et al. |
| 2013/0268062 | A1 | 10/2013 | Puckett et al. |
| 2014/0324141 | A1 | 10/2014 | Arnholt et al. |
| 2015/0025608 | A1 | 1/2015 | Delaney et al. |
| 2015/0088238 | A1 | 3/2015 | Arnholt et al. |
| 2015/0343200 | A1 | 12/2015 | Arnholt et al. |

FOREIGN PATENT DOCUMENTS

| | | | |
|---|---|---|---|
| JP | 2004119113 A | 4/2004 | |
| JP | 2007154336 A | 6/2007 | |
| JP | 2008515611 A | 5/2008 | |
| JP | 2008253297 A | 10/2008 | |
| JP | 2009000100 A | 1/2009 | |
| JP | 2009507577 A | 2/2009 | |
| JP | 2009531140 A | 9/2009 | |
| JP | 2009535182 A | 10/2009 | |
| JP | 2009540873 A | 11/2009 | |
| JP | 2010540105 A | 12/2010 | |
| SU | 132800 A | 1/1960 | |
| WO | WO9908466 A1 | 8/1990 | |
| WO | WO02089909 A1 | 11/2002 | |
| WO | WO03045875 A1 | 6/2003 | |
| WO | WO03101505 A1 | 12/2003 | |
| WO | WO2004041529 A1 | 5/2004 | |
| WO | WO2005032400 A2 | 4/2005 | |
| WO | WO2005039664 A2 | 5/2005 | |
| WO | WO2005065578 A2 | 7/2005 | |
| WO | WO2005079339 A2 | 9/2005 | |
| WO | WO2006020425 A1 | 2/2006 | |
| WO | 2006041767 A2 | 4/2006 | |
| WO | WO2006123340 A2 | 11/2006 | |
| WO | WO2007003199 A1 | 1/2007 | |
| WO | WO2007030722 A1 | 3/2007 | |
| WO | WO2007109007 A1 | 9/2007 | |
| WO | WO2007130900 A2 | 11/2007 | |
| WO | WO2008008266 A2 | 1/2008 | |
| WO | WO2008021020 A2 | 2/2008 | |
| WO | WO2008036460 A1 | 3/2008 | |
| WO | WO2008055038 A2 | 5/2008 | |
| WO | WO2008060333 A1 | 5/2008 | |
| WO | WO2008066538 A1 | 6/2008 | |
| WO | WO2008066912 A2 | 6/2008 | |
| WO | WO2008066914 A1 | 6/2008 | |
| WO | WO2009002984 A2 | 12/2008 | |
| WO | WO2009140381 A1 | 11/2009 | |
| WO | 2010053585 A1 | 5/2010 | |
| WO | 2010107967 A1 | 9/2010 | |
| WO | WO2010065484 A1 | 10/2010 | |
| WO | 2011017695 A1 | 2/2011 | |
| WO | 2011017698 A1 | 2/2011 | |
| WO | 2011028873 A2 | 3/2011 | |
| WO | 2013025465 A1 | 2/2013 | |
| WO | 2013112793 A1 | 8/2013 | |
| WO | 2013151778 A1 | 10/2013 | |

OTHER PUBLICATIONS

Jhuna Datta, et al., Cocrystallization of poly(vinylidene fluoride) and vinylidene fluoridetetrafluoro-ethylene copolymer blends: 3. Structural study, Polymer Science Unit, Indian Association for the Cultivation of Science, Jadavpur, Calcutta—700032, India, Polymer vol. 38 No. 11, 1997, Elsevier Science Ltd, pp. 2719-2724.

Mercedes Perez De Obanos, et al., Selective Corrosion of Pvdf crystalline Structures by Sodium Hydroxide, Sep. 2001, Revista de la Facultad de Ingenieria de la U.C.V., vol. 16, No. 2, pp. 95-103, English Abstract, pp. 95-96.

Kin Liu, et al, In vivo wound healing and antibacterial performances of electrospun nanofibre membranes, 2010 Wiley Periodicals, Inc., Journal of Biomedical Materials Research A | Aug. 2010 vol. 94A, Issue 2, pp. 499-508.

Wikipedia. "Gel," [Online], Page last modified Jan. 1, 2017, retrieved from the Internet <https://en.wikipedia.org/wiki/Gel>, 7 pages.

de Navarro, C. Urbina, et al. Contribución Al Estudio De Los Factores Que Influyeron En Falla De Tuberías De PVDF. Acta Microscópica, 13(1):55-61, 2004, [English Abstract].

de Navarro, C. Urbina, et al. Relationship Between the Degradation of PVDF and the Presence of Crystalline Phases Alpha and the Mixed. CIASEM 201: 11th Inter American Congress on Microscopy, E.R.R.B.A.A.O. (UAY), Editor 2011, Merida Yucatan, Mexico.

He, Fuan, et al. Preparation and Characterization of Electrospun Poly(Vinylidene Fluoride)/Poly(Methyl Methacrylate) Membrane. High Performance Polymers, 26(7):817-825, 2014.

Hong, Lingfei; Pan, Tingrui, "Photopatternable Superhydrophobic Nanocomposites for Microfabrication," Journal of Microelectromechanical Systems, vol. 19, No. 2, (Apr. 2010), pp. 246-253.

Huang, Zheng-Ming et al., "A review on polymer nanofibers by electrospinning and their applications in nanocomposites", Composites Science and Technology, No. 66, 2003, pp. 2223-2253.

International Preliminary Report on Patentability, Chapter II, issued in PCT/US2012/050260, completed Oct. 28, 2013, 16 pages.

International Preliminary Report on Patentability, Chapter II, issued in PCT/US2012/065896, dated Dec. 18, 2013, 8 pages.

International Search Report arid Written Opinion issued in PCT/US2012/050260, dated Dec. 7, 2012, 12 pages.

International Search Report and Written Opinion issued in PCT/US2012/065896, dated Feb. 20, 2013, 9 pages.

Lee, J. L., "Polymer Nanoengineering for Biomedical Applications", Annals of Biomedical Engineering,34(1), (2006), 75-88.

Menini, Richard, et al., "Production of superhydrophobic polymer fibers with embedded particles using the electrospinning technique," Society of Chemical Industry, Polym Int 57, pp. 77-84 (2008). DOI: 10.1002/pi.

Ostwald, W. Studien Uber Die Bildung und Umwandlung Fester Korper—1. Abhandlung: Ubersattingung und Uberkaitung, Zietschrift f. physik. Chemie. XXII. Leipzig, Physiko-chemisches Laboratorium, Feb. 1897, pp. 289-330.

Ross, G. J., et al. Surface Modification of Poly(Vinylidene Fluoride) by Alkaline Treatment Part 2. Process Modification by the Use of Phase Transfer Catalysts. Polymer 42:403-413, 2001.

(56) References Cited

OTHER PUBLICATIONS

Ross, G. J., et al. Surface Modification of Poly(Vinylidene Fluoride) by Alkaline Treatment: 1. The Degradation Mechanism. Polymer 41:1685-1696, 2000.
Su, Ching-luan et al., "A Study of Hydrophobic Electrospun Membrane Applied in Seawater Desalination by Membrane Distillation," Fibers and Polymers (2012), vol. 13, No. 6, pp. 698-702. DOI 10.1007/s12221-012-0698-3.
Written Opinion of the International Preliminary Examining Authority issued in PCT/US2012/050260, dated Jul. 18, 2013; 7 pages.
Zhou, Tao; Yao, Yongyi; Xiang, Ruili; Wu, Yurong, "Formation and characterization of polytetrafluoroethylene nanofiber membranes for vacuum membrane distillation," Journal of Membrane Science 453 (2014), pp. 402-408. <www.elsevier.com/locate/memsci>.

* cited by examiner

MEDICAL ELECTRICAL LEAD WITH BIOSTABLE PVDF-BASED MATERIALS

CROSS-REFERENCE TO RELATED APPLICATION

This application claims priority to Provisional Application No. 62/197,000, filed Jul. 25, 2015, which is herein incorporated by reference in its entirety.

TECHNICAL FIELD

The present invention relates to medical devices. More specifically, the invention relates to medical electrical leads and methods manufacturing medical electrical leads.

BACKGROUND

Cardiac pacing leads are well known and widely employed for carrying pulse stimulation signals to the heart from a battery operated pacemaker, or other pulse generating means, as well as for monitoring electrical activity of the heart from a location outside of the body. Electrical energy is applied to the heart via an electrode to return the heart to normal rhythm. Some factors that affect electrode performance include polarization at the electrode/tissue interface, electrode capacitance, sensing impedance, and voltage threshold. In all of these applications, it is highly desirable to optimize electrical performance characteristics at the electrode/tissue interface.

Recognized performance challenges of materials conventionally used as electrodes include difficulty controlling tissue in-growth, inflammation in the vicinity of the implanted device and/or the formation of fibrous scar tissue. These challenges may lead to difficulty in extracting the lead and/or reduced electrode performance over time.

SUMMARY

Example 1 is a medical electrical lead including an insulative lead body extending from a distal region to a proximal region, a conductor disposed within the insulative lead body and extending from the proximal region to the distal region, an electrode disposed on the insulative lead body and in electrical contact with the conductor, and a fibrous matrix disposed on at least part of the electrode. The fibrous matrix includes fibers. The fibers include a polyvinylidene fluoride-based (PVDF-based) polymer and a crystal-modifying additive. The PVDF-based polymer includes an amorphous PVDF phase and a crystalline PVDF phase. The crystalline PVDF phase includes a beta form crystalline structure in an amount exceeding any other crystalline structure form in the crystalline PVDF phase.

In Example 2, the medical electrical lead of Example 1, wherein the PVDF-based polymer is polyvinylidene fluoride.

In Example 3, the medical electrical lead of Example 1, wherein the PVDF-based polymer is poly(vinylidene fluoride-co-hexafluoropropylene).

In Example 4, the medical electrical lead of any of Examples 1-3, wherein the additive includes a polymer that is miscible with the PVDF-based polymer.

In Example 5, the medical electrical lead of any of Examples 1-4, wherein the additive includes at least one of polyacrylonitrile, poly(butyl methacrylate), polycaprolactone, poly(methyl methacrylate), polysulfone, and polyvinyl chloride.

In Example 6, the medical electrical lead of Example 5, wherein the additive includes poly(methyl methacrylate).

In Example 7, the medical electrical lead of any of Examples 1-6, wherein the fibrous matrix further includes a coating of a material that increases the wettability of the fibers as compared to uncoated fibers.

In Example 8, the medical electrical lead of Example 7, wherein the material is poly(ethylene glycol dimethacrylate).

In Example 9, the medical electrical lead of any of Examples 1-8, wherein the crystalline PVDF phase further includes an alpha form crystalline structure and a ratio of the beta form to the alpha form is at least about 50 to 1.

In Example 10, the medical electrical lead of Example 9, wherein the crystalline PVDF phase is substantially free of the alpha form crystalline structure.

Example 11 is a method of forming a medical electrical lead having the insulative lead body and the electrode disposed on the insulative lead body according to any of claims 1-10. The method includes forming a blend of the polyvinylidene fluoride-based (PVDF-based) polymer and the crystal-modifying additive miscible with the PVDF-based polymer, electro-spinning the blend to form the fibrous matrix, disposing the fibrous matrix at least partially over the electrode, and sintering the fibrous matrix at a temperature between 110° C. and 150°, wherein after sintering the PVDF-based polymer includes the beta form crystalline structure in an amount exceeding any other crystalline structure form in the crystalline PVDF phase.

In Example 12, the method of Example 11, further including coating the fibrous matrix with a material that increases the wettability of the fibrous matrix as compare to an uncoated fibrous matrix.

In Example 13, the method of any of Examples 11-12, wherein the sintering is for a time ranging from 10 minutes to 20 minutes.

In Example 14, the method of any of Examples 11-13, further including adding a solvent to the blend before electro-spinning.

In Example 15, the method of any of Examples 11-14, further including adding a metal salt solution to the blend before electro-spinning.

Example 16 is medical electrical lead including an insulative lead body extending from a distal region to a proximal region, a conductor disposed within the insulative lead body and extending from the proximal region to the distal region, an electrode disposed on the insulative lead body and in electrical contact with the conductor, and a fibrous matrix disposed on at least part of the electrode. The fibrous matrix includes fibers. The fibers include a polyvinylidene fluoride-based (PVDF-based) polymer and a crystal-modifying additive. The PVDF-based polymer includes an amorphous PVDF phase and a crystalline PVDF phase. The crystalline PVDF phase includes a beta form crystalline structure in an amount exceeding any other crystalline structure form in the crystalline PVDF phase, and the crystalline PVDF phase is substantially free of an alpha form crystalline structure.

In Example 17, the medical electrical lead of Example 16, wherein the PVDF-based polymer is polyvinylidene fluoride.

In Example 18, the medical electrical lead of Example 16, wherein the PVDF-based polymer is poly(vinylidene fluoride-co-hexafluoropropylene).

In Example 19, the medical electrical lead of any of Examples 16-18, wherein the additive includes a polymer that is miscible with the PVDF-based polymer.

In Example 20, the medical electrical lead of any of Examples 16-19, wherein the additive includes at least one of polyacrylonitrile, poly(butyl methacrylate), polycaprolactone, poly(methyl methacrylate), polysulfone, and polyvinyl chloride.

In Example 21, the medical electrical lead of any of Examples 16-20, wherein the additive includes poly(methyl methacrylate).

In Example 22, the medical electrical lead of Examples 16-21, wherein the fibrous matrix further includes a coating of a material that increases the wettability of the fibers as compared to uncoated fibers.

In Example 23, the medical electrical lead of Example 22, wherein the material is poly(ethylene glycol) dimethacrylate.

Example 24 is a method of forming a medical electrical lead having an insulative lead body and an electrode disposed on the insulative lead body. The method includes forming a blend of a polyvinylidene fluoride-based (PVDF-based) polymer and a crystal-modifying additive miscible with the PVDF-based polymer, electro-spinning the blend to form a fibrous matrix, disposing the fibrous matrix at least partially over the electrode, and sintering the fibrous matrix. The fibrous matrix is sintered at a temperature between 110° C. and 150° C. for a time ranging from 10 minutes to 20 minutes, wherein after sintering the PVDF-based polymer includes a beta form crystalline structure in an amount exceeding any other crystalline structure form in the crystalline PVDF phase.

In Example 25, the method of Example 24, further including coating the fibrous matrix with a material that increases the wettability of the fibrous matrix as compare to an uncoated fibrous matrix.

In Example 26, the method of Example 25, wherein the material is poly(ethylene glycol) dimethacrylate.

In Example 27, the method of any of Examples 24-26, wherein the PVDF based polymer is polyvinylidene fluoride.

In Example 28, the method of any of Examples 24-26, wherein the PVDF-based polymer is poly(vinylidene fluoride-co-hexafluoropropylene).

In Example 29, the method of any of Examples 24-28, wherein the additive includes at least one of polyacrylonitrile, poly(butyl methacrylate), polycaprolactone, poly(methyl methacrylate), polysulfone, and polyvinyl chloride.

In Example 30, the method of any of Examples 24-29, wherein the additive includes poly(methyl methacrylate).

Example 31 is a medical electrical lead including an insulative lead body extending from a distal region to a proximal region, a conductor disposed within the insulative lead body and extending from the proximal region to the distal region, an electrode disposed on the insulative lead body and in electrical contact with the conductor, and a fibrous matrix disposed on at least part of the electrode. The fibrous matrix includes electrospun fibers. The fibers include a polyvinylidene fluoride-based (PVDF-based) polymer and a crystal-modifying additive. The PVDF-based polymer includes an amorphous PVDF phase and a crystalline PVDF phase. The crystalline PVDF phase includes a beta form crystalline structure in an amount exceeding any other crystalline structure form in the crystalline PVDF phase.

In Example 32, the medical electrical lead of Example 31, wherein the additive includes at least one of polyacrylonitrile, poly(butyl methacrylate), polycaprolactone, poly(methyl methacrylate), polysulfone, and polyvinyl chloride.

In Example 33, the medical electrical lead of any of Examples 31-32, wherein the PVDF-based polymer is a poly(vinylidene fluoride-co-hexafluoropropylene), and the additive includes poly(methyl methacrylate).

In Example 34, the medical electrical lead of any of Examples 31-33, wherein the fibrous matrix further includes a coating of a material that increases the wettability of the fibers as compared to uncoated fibers.

In Example 35, the medical electrical lead of any of Examples 31-34, wherein the crystalline PVDF phase further includes an alpha form crystalline structure and a ratio of the beta form to the alpha form is at least about 50 to 1.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
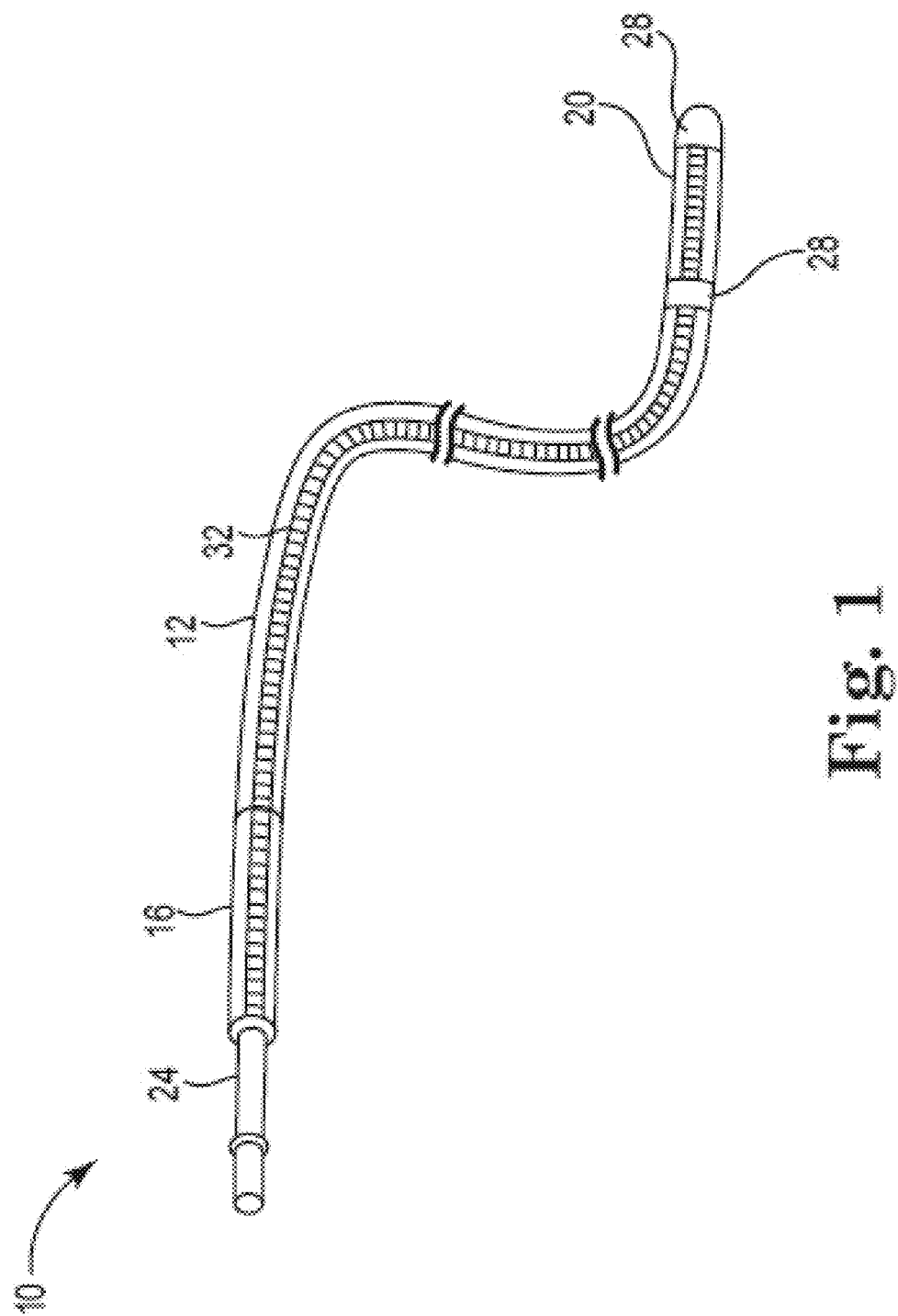
FIG. 1 is a schematic view of a medical electrical lead according to embodiments of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

A more complete understanding of the present invention is available by reference to the following detailed description of numerous aspects and embodiments of the invention. The detailed description of the invention which follows is intended to illustrate but not limit the invention.

Difficulties associated with controlling tissue in-growth, the formation of fibrous scar tissue, and/or inflammation in the vicinity of an electrode of a medical electrical lead may be overcome by the use of a fibrous matrix over the electrode as described in "METHOD FOR COATING DEVICES USING ELECTROSPINNING AND MELT BLOWING" (U.S. Pat. No. 8,903,506, issued Dec. 2, 2014), hereby incorporated by reference in its entirety. Such fibrous matrices may be formed from a non-conductive fluoropolymer material. Suitable fluoropolymer materials may include polyvinylidene fluoride-based (PVDF-based) materials, for example, polyvinylidene fluoride (PVDF) and/or poly(vinylidene fluoride-co-hexafluoropropylene) (PVDF-HFP). Such fluoropolymer materials are known for their abrasion resistance and chemical resistance.

FIG. 1 provides an illustrative but non-limiting example of a medical application using a medical electrical lead. The application and location are illustrative only, as medical electrical leads incorporating embodiments of the present invention may be used in a variety of anatomical locations and for a variety of additional purposes.

FIG. 1 is a partial cross-sectional view of a medical electrical lead 10, in accordance with various embodiments of the present disclosure. According to some embodiments, the medical electrical lead 10 can be configured for implantation within a patient's heart. According to other embodiments, the medical electrical lead 10 is configured for implantation within a patient's neurovascular regions. In yet another embodiment, the lead 10 can be a lead for a cochlear implant. The medical electrical lead 10 includes an elongated, insulative lead body 12 extending from a proximal end 16 to a distal end 20. The proximal end 16 is configured to be operatively connected to a pulse generator via a connector 24. At least one conductor 32 extends from the connector 24 at the proximal end 16 of the lead 10 to one or more electrodes 28 at the distal end 20 of the lead 10. The conductor 32 can be a coiled or cable conductor. According to some embodiments where multiple conductors are employed, the lead can include a combination of coiled and cable conductors. When a coiled conductor is employed, according to some embodiments, the conductor can have either a co-radial or a co-axial configuration.

The medical electrical lead 10 can be unipolar, bipolar, or multi-polar depending upon the type of therapy to be delivered. In embodiments of the present disclosure employing multiple electrodes 28 and multiple conductors 32, each conductor 32 is adapted to be connected to an individual electrode 28 in a one-to-one manner allowing each electrode 28 to be individually addressable. Additionally, the lead body 12 can include one or more lumens adapted to receive a guiding element such as a guide wire or a stylet for delivery of the lead 10 to a target location within a patient's heart.

The electrodes 28 can have any electrode configuration as is known in the art. According to one embodiment of the present disclosure, at least one electrode can be a ring or partial ring electrode. According to another embodiment, at least one electrode 28 is a shocking coil. According to yet another embodiment of the present disclosure, at least one electrode 28 includes an exposed electrode portion and an insulated electrode portion. In some embodiments, a combination of electrode configurations can be used. The electrodes 28 can be coated with or formed from platinum, stainless steel, titanium, tantalum, palladium, MP35N, other similar conductive material, alloys of any of the foregoing including platinum-iridium alloys, and other combinations of the foregoing including clad metal layers or multiple metal materials.

Figure 2A:
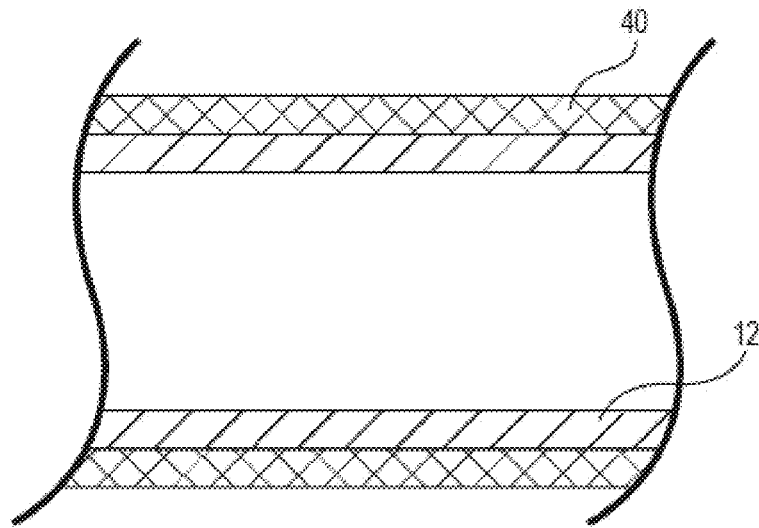
FIGS. 2A and 2B are schematic longitudinal cross-sections of a medical electrical lead according to embodiments of the present invention.
Figure 2B:
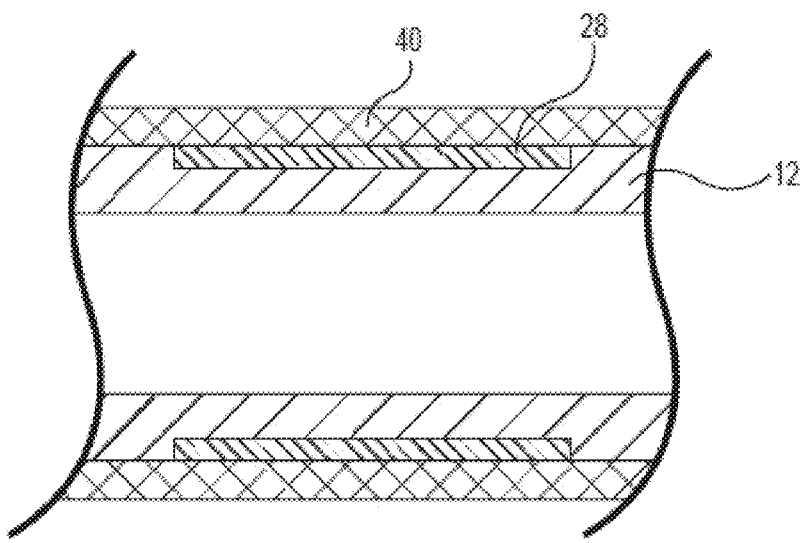

The lead 10 includes a fibrous matrix that is disposed over various parts of the insulative lead body 12. FIGS. 2A and 2B provide illustrative but non-limiting examples of regions of the lead 10 that may include a fibrous matrix. FIGS. 2A and 2B are schematic longitudinal cross-sectional views of the lead 10 of FIG. 1, in which internal structure has been removed for clarity.

FIG. 2A shows a fibrous matrix 40 disposed over a portion of the insulative lead body 12. The illustrated portion of the insulative lead body 12 may be adjacent an electrode such as the electrode 28, or it may be spaced apart from the electrodes. In contrast, FIG. 2B illustrates a fibrous matrix 40 disposed over the electrode 28. While the fibrous matrix 40 is illustrated as covering all of the electrode 28, in some embodiments the fibrous matrix 40 covers only a small portion of the electrode 28, a substantial portion of the electrode 28, or an intervening fraction of the electrode 28.

In some embodiments, the fibrous matrix 40 may provide various beneficial functionalities to the lead 10. In some embodiments, the fibrous matrix 40 may improve the abrasion resistance of the lead 10. In some embodiments, the fibrous matrix 40 may improve the electrical or thermal insulation of the lead 10. In some embodiments, the fibrous matrix 40 may provide improved control over tissue ingrowth, particularly at the site of the electrode 28. In certain embodiments, the amount of tissue ingrowth may be determined by tissue extraction in which the force required to remove an implanted lead 10 is measured with an Instron force gauge. In some embodiments, the thickness and average fiber diameter of fibrous matrix 40 impacts tissue ingrowth. The thickness and average fiber diameter of fibrous matrix 40 may also impact the ability to deliver electrophysiological therapy through fibrous matrix 40. In certain embodiments, the fibrous matrix 40 does not significantly impact the impedance of the lead 10.

The fibrous matrix 40 includes a plurality of randomly aligned fibers that comprise the matrix. In certain embodiments the fibrous matrix 40 may be formed by electrospinning, for example. The fibers may have diameters in the range of about 10-3000 nanometers (nm), for example. The fiber diameter size may be about 40-2000 nm, about 50-1500 nm or about 100-1000 nm, for example. The fiber diameter size may be measured by taking the average size of the fibers. In certain embodiments, the fibers may have diameters as little as 40 nm, 50 nm, 100 nm or 150 nm and as great as 300 nm, 400 nm, 500 nm, 600 nm, 650 nm, 700 nm, 725 nm, 750 nm or 800 nm or may be within any range delimited by any pair of the foregoing values. In other embodiments, the fibers may have an average diameter size less than about 800 nm, 750 nm, 725 nm, 700 nm, 600 nm, 500 nm or 400 nm. In other embodiments, the fiber matrix 40 may be formed partially or completely with hollow fibers using modified electrospinning techniques.

The fibrous matrix 40 may have an average fiber-to-fiber-spacing in the range of about 1 to about 100 microns, more particularly from about 10 to about 50 microns, even more particularly from about 10 to about 25 microns. In some embodiments, the fiber spacing between adjacent fibers may be adjusted or regulated to control tissue ingrowth while minimizing impact on pacing capability. This can be accomplished, for example, by altering the deposition parameters or deposition material. In other embodiments, tissue in-growth is controlled by the thickness of the matrix. Suitable thicknesses for the fibrous matrix may range from about 0.00254 millimeters (mm) to about 0.254 mm (about 0.0001 inches (in.) to about 0.01 in.), more particularly from about 0.0127 mm to about 0.127 mm (about 0.0005 in. to about 0.005 in.), even more particularly from about 0.0254 mm to about 0.0762 mm (about 0.001 in. to about 0.003 in.).

In some embodiments, particularly when the fibrous matrix 40 is disposed over an electrode such as the electrode 28, the fibrous matrix 40 may have sufficient fiber spacing to permit ions from fluids within and around the tissues adjacent to the fibrous matrix 40 to flow through the fibrous matrix 40. The flow of ions may provide electrical contact between the electrode 28 and the tissues and enable delivery of electrophysiological therapy and/or sensing of electrical conditions adjacent to the medical electrical lead 10.

The fluids within and around the tissues are known to be mildly corrosive due in part to an oxidative effect of the body's immune system. Materials and devices for use in this environment may be evaluated for biostability by exposure to a solution of hydrogen peroxide and cobalt (II) chloride at an elevated temperature. The cobalt (II) chloride catalyzes the oxidation reaction of hydrogen peroxide, producing an accelerated oxidative stress test environment. Such a solution may include, for example, a mixture of a 3% hydrogen peroxide solution and 0.1 M cobalt (II) chloride solution.

A fibrous matrix including a PVDF-based polymer, PVDF-HFP, disposed over an electrode was subjected to the aforementioned solution at a temperature of 70° C. for 14 days. Surprisingly, following this oxidative stress test, the fibrous matrix was observed to have failed in that most of the fibrous matrix was completely removed from the electrode surface. This was particularly unexpected as PVDF-based polymers are generally known for resisting much more severe chemical exposures.

Portions of the fibrous matrix that remained following the oxidative stress test were analyzed and compared to samples of a fibrous matrix including the PVDF-based polymer before oxidative stress testing. PVDF may be a mixture of an amorphous phase interspersed with a crystalline phase. The crystalline phase of PVDF may include up to five crystalline form structures known as alpha, beta, gamma, delta, and epsilon. The alpha form crystalline structure, according to Formula I below, is generally the most common form as it is the most thermodynamically favorable crystalline structure.

Formula I

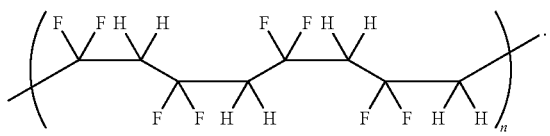

X-ray powder diffraction analysis was employed to determine any differences in the crystalline structure between initial samples of the PVDF-based polymer and the PVDF-based polymer portions that survived the oxidative stress testing. The x-ray powder diffraction analysis revealed that the portions of the fibrous matrix to have survived the oxidative stress test had much less of the alpha form crystalline structure than the PVDF-based polymer before the oxidative stress testing. Without wishing to be bound by any theory, it is believed that the alpha form crystalline structure was chemically attacked and removed during the oxidative stress test, thus causing the failure of the fibrous matrix.

In some embodiments, the plurality of randomly aligned fibers that comprise the fiber matrix 40 include a PVDF-based polymer having an amorphous PVDF phase and a crystalline PVDF phase. Both the amorphous PVDF phase and the crystalline PVDF phase may be distributed throughout the fibrous matrix 40. In some embodiments, the beta form crystalline structure, according to Formula II below, is present in an amount exceeding any other crystalline structure form in the crystalline PVDF phase.

Formula II

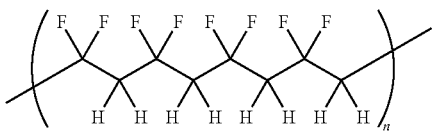

The beta form crystalline structure may not be as susceptible to chemical attack as the alpha form. The predominance of the beta form crystalline structure in the fiber matrix 40 results in less of the alpha form, and may result in less susceptibility of the fiber matrix 40 to attack by oxidative stress and provide improved biostability. In some embodiments, the crystalline PVDF phase includes beta and alpha form crystalline structures in a ratio of beta to alpha of about 50 to 1, 100 to 1, 500 to 1, or 1000 to 1. In some embodiments, the crystalline PVDF phase may be substantially free of the alpha form crystalline structure. Substantially free means the alpha form crystalline structure is not detectable by techniques used for determining the presence and relative amounts of the crystalline structure forms. The presence and relative amounts of alpha and beta form crystalline structures making up the crystalline PVDF phase may be determined by, for example, Fourier transform infrared spectroscopy (FTIR).

The fibrous matrix 40 may also include a crystal-modifying additive. The crystal-modifying additive may be miscible with the PVDF-based polymer. Examples of crystal-modifying additives miscible with the PVDF-based polymer include polyacrylonitrile (PAN), poly(butyl methacrylate) (PBMA), polycaprolactone (PCL), poly(methyl methacrylate) (PMMA), polysulfone (PSF), and polyvinyl chloride (PVC). In other embodiments, the crystal-modifying additive may include an organic functionalized nanoclay or hematite nanoparticles. In some embodiments, the crystal-modifying additive may be present in the fiber matrix 40 in an amount as little as about 1 weight percent (wt. %), about 2 wt. %, about 5 wt. %, or as great as about 10 wt. %, about 20 wt. %, or about 30 wt. %, or may be present within any range defined between any pair of the foregoing values. In exemplary embodiments, the crystal-modifying additive may be present in the fiber matrix 40 in an amount from about 1 wt. % to about 30 wt. %, from about 2 wt. % to about 20 wt. %, or from about 5 wt. % to about 10 wt. %. In some exemplary embodiments, the crystal-modifying additive may be present in the fiber matrix 40 in an amount of about 7 wt. %.

Fibers made of PVDF-based polymers may be hydrophobic and therefore, less susceptible to attack by the oxidative stress test because hydrophobicity inhibits the flow of corrosive fluids through the fiber matrix 40. However, the hydrophobicity also prevents or impedes the flow of ions through the fiber matrix 40, limiting the electrical contact between the electrode 28 and adjacent tissues and interfering with the delivery of electrophysiological therapy. In some embodiments, the fibers of fibrous matrix 40 may further include a coating of a material that increases the wettability of fibers as compared to uncoated fibers. The material may include, for example, poly(ethylene glycol) or poly(ethylene glycol) dimethacrylate. Fibers coated with the material may be hydrophilic, thus providing little or no barrier to the flow of ions through the fiber matrix 40, and allowing the delivery of electrophysiological therapy and/or sensing of electrical conditions adjacent to the medical electrical lead 10. In such embodiments, it may be particularly useful that the beta form crystalline structure is present in the fiber matrix 40 in an amount exceeding any other crystalline structure form in the crystalline PVDF phase resulting in less of the alpha form, and less susceptibility to attack by oxidative stress.

The fibrous matrix 40 may be prepared from a blend of a PVDF-based polymer and a crystal modifying additive, as described above. The blend may then be electrospun to form the fibrous matrix 40, as describe below in reference to FIG. 3. In some embodiments, the medical electrical lead 10 may be assembled before the fibrous matrix 40 is formed directly on at least part of the electrode 28. In some embodiments, the fibrous matrix 40 may be formed on at least part of the electrode 28 before the medical electrical lead 10 is assembled. In some embodiments, the fibrous matrix 40 may be separately formed and then subsequently disposed onto at least a part of the electrode 28.

In some embodiments, the fibrous matrix 40 may be sintered to stabilize the characteristics of the fibrous matrix 40. In some embodiments, the fibrous matrix 40 may be sintered before being disposed at least partially over the electrode 28. In other embodiments, the fibrous matrix 40 may be sintered after being disposed at least partially over the electrode 28. The fibrous matrix 40 may be sintered at temperatures as low as about 110° C., or about 120° C., or as great as about 140° C., or about 150° C., or at a temperature within any range defined between any pair of the foregoing values. In exemplary embodiments, the fibrous matrix 40 may be sintered at a temperature from about 110° C. to about 150° C., or about 120° C. to about 140° C. In some exemplary embodiments, the fiber matrix 40 may be sintered at a temperature of about 130° C. In some embodiments, the fiber matrix 40 may be sintered for a time as little as about 10 minutes, about 12 minutes, or about 14 minutes, or as great as about 16 minutes, about 18 minutes, or about 20 minutes, or a time between within any range defined between any pair of the foregoing values. In exemplary embodiments, the fiber matrix 40 may be sintered for a time from about 10 minutes to about 20 minutes, about 12 minutes to about 18 minutes, or about 14 minutes to about 16 minutes. In some exemplary embodiments, the fiber matrix 40 may be sintered for about 15 minutes.

In some embodiments, after sintering step, the PDVF-based polymer of the fiber matrix 40 may include the beta form crystalline structure in an amount exceeding any other crystalline structure form in the crystalline PVDF phase. In some embodiments, after the sintering step, the crystalline PVDF phase may include beta and alpha form crystalline structures in a ratio of beta to alpha of about 50 to 1, 100 to 1, 500 to 1, or 1000 to 1. In some embodiments, the crystalline PVDF phase may be substantially free of the alpha form crystalline structure. Not wishing to be bound by any particular theory, it is believed that the electrospinning process produces PVDF in which the beta form crystalline structure predominates. The crystal-modifying additive interferes with the formation of the alpha form crystalline structure, which may otherwise occur during the sintering step. Without the crystal-modifying additive, it is believed that the sintering process would transform some of the beta form crystalline structure to the alpha form crystalline structure, thus increasing the susceptibility of the fiber matrix 40 to chemical attack.

Figure 3:
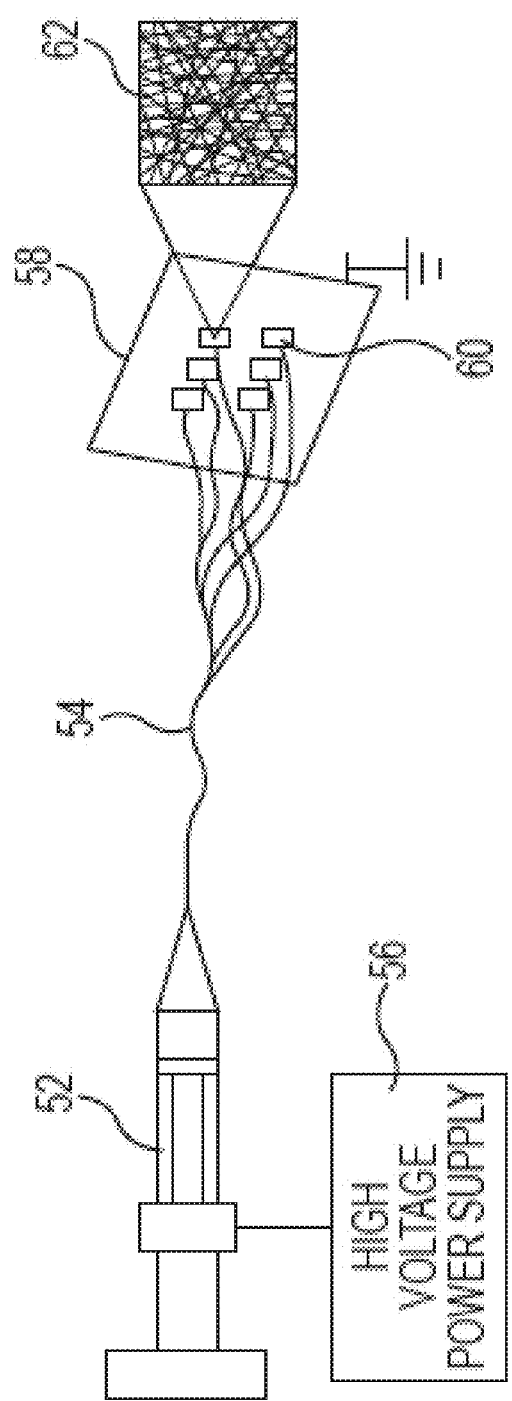
FIG. 3 is a schematic illustration of electrospinning.

FIG. 3 provides a schematic illustration of electrospinning. An electric field may be used to draw a polymer solution or melt 54 from a capillary source 52. In some embodiments, the capillary source 52 may be a syringe. The polymer solution or melt 54 is drawn to a grounded collector 58. A high voltage power supply 56 may be used to power the process. The elements 60 to be coated may be placed on the collector 58 to be coated. Upon drying, a thin polymeric web 62 may be formed. In some embodiments, the fiber sizes may be controlled by adjusting the relative concentration of polymer in the polymer solution or melt 54.

The concentration of polymer in the electrospinning solution and solvent selection are important factors in achieving desired fibrous matrix properties, and in particular for controlling porosity and/or fiber size. Additionally, a small amount of a metal salt solution may be added to the electrospinning solution to improve deposition. In other embodiments, the electrospinning solution has a polymer concentration of between about 1 wt. % and about 40 wt. %, more particularly between about 1 wt. % and about 30 wt. %, even more particularly from about 3 wt. % to about 15 wt. %, and even more particularly from about 5 wt. % to about 15 wt. %. Suitable solvents include dimethylformamide, dimethylacetamide, N-methyl-2-pyrrolidone, dimethyl sulfoxide, acetone, cyclohexane tetrohydrofuran as well as mixtures and co-solvents thereof.

Although the description herein discusses the fibrous matrix 40 on a lead 40, fibrous matrix 40 may be on any medical electrical device such as but not limited to implantable electrical stimulation systems including neurostimulation systems such as spinal cord stimulation (SCS) systems, deep brain stimulation (DBS) systems, peripheral nerve stimulation (PNS) systems, gastric nerve stimulation systems, cochlear implant systems, and retinal implant systems, among others, and cardiac systems including implantable cardiac rhythm management (CRM) systems, implantable cardioverter-defibrillators (ICD's), and cardiac resynchronization and defibrillation (CRDT) devices, among others.

EXAMPLE

The present invention is more particularly described in the following example that is intended as an illustration only, since numerous modifications and variations within the scope of the present invention will be apparent to those of skill in the art.

A mixture of 90 wt. % polyvinylidene fluoride (PVDF) and 10 wt. % poly(methyl methacrylate) (PMMA) was blended into a solvent mixture of 80 vol. % dimethylformamide and 20 vol. % acetone. The PVDF/PMMA mixture was 22.5 wt. % of the resulting solution.

Figure 4:
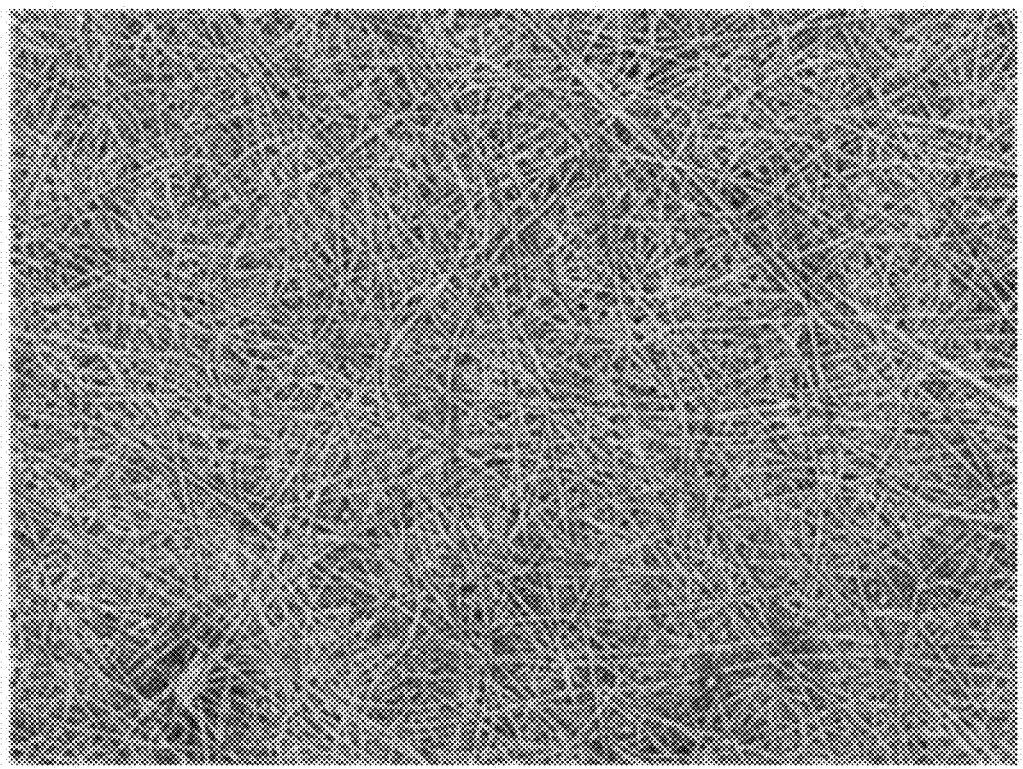
FIG. 4 is an image of a thin polymeric web of polyisobutylene-polyurethane block copolymer formed on an electrode of a medical electrical lead in accordance with embodiments of the present invention.

The PVDF/PMMA solution was loaded into a syringe and connected to a nozzle of an electrospinning machine. The PVDF/PMMA solution was electrospun at a flow rate of 0.3 milliliters per hour onto an electrode of a medical electrical lead positioned 10 cm from a tip of the nozzle to form a polymeric web on the electrode. Ambient conditions included a relative humidity of 34% and a temperature of 20° C. FIG. 4 is an image of the resulting thin polymeric web of PVDF/PMMA magnified 1000 times.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:
1. A medical electrical lead comprising:
an insulative lead body extending from a distal region to a proximal region;
a conductor disposed within the insulative lead body and extending from the proximal region to the distal region;
an electrode disposed on the insulative lead body and in electrical contact with the conductor; and
a fibrous matrix disposed on at least part of the electrode, the fibrous matrix including fibers, the fibers including:
a polyvinylidene fluoride-based (PVDF-based) polymer including an amorphous PVDF phase and a crystalline PVDF phase, wherein the crystalline PVDF phase includes a beta form crystalline structure in an amount exceeding any other crystalline structure form in the crystalline PVDF phase; and
a crystal-modifying additive.

2. The medical electrical lead of claim 1, wherein the PVDF-based polymer is polyvinylidene fluoride.

3. The medical electrical lead of claim 1, wherein the PVDF-based polymer is poly(vinylidene fluoride-co-hexafluoropropylene).

4. The medical electrical lead of claim 1, wherein the crystal-modifying additive includes a polymer that is miscible with the PVDF-based polymer.

5. The medical electrical lead of claim 1, wherein the crystal-modifying additive includes at least one of polyacrylonitrile, poly(butyl methacrylate), polycaprolactone, poly(methyl methacrylate), polysulfone, and polyvinyl chloride.

6. The medical electrical lead of claim 5, wherein the crystal-modifying additive includes poly(methyl methacrylate).

7. The medical electrical lead claim 1, wherein the fibrous matrix further includes a coating containing a material that increases the wettability of the fibers as compared to uncoated fibers.

8. The medical electrical lead of claim 7, wherein the material is poly(ethylene glycol dimethacrylate).

9. The medical electrical lead of claim 1, wherein the crystalline PVDF phase further includes an alpha form crystalline structure and a ratio of the beta form crystalline structure to the alpha form crystalline structure is at least about 50 to 1.

10. A method of forming a medical electrical lead having an insulative lead body extending from a distal region to a proximal region, a conductor disposed within the insulative lead body and extending from the proximal region to the distal region, an electrode disposed on the insulative lead body and in electrical contact with the conductor, and a fibrous matrix disposed on at least part of the electrode, the fibrous matrix including fibers, the fibers including a polyvinylidene fluoride-based (PVDF-based) polymer including an amorphous PVDF phase and a crystalline PVDF phase, the crystalline PVDF phase including a beta form crystalline structure in an amount exceeding any other crystalline structure form in the crystalline PVDF phase, and a crystal-modifying additive, the method comprising:
   forming a blend of the polyvinylidene fluoride-based (PVDF-based) polymer and the crystal-modifying additive miscible with the PVDF-based polymer;
   electro-spinning the blend to form the fibrous matrix;
   disposing the fibrous matrix at least partially over the electrode; and
   sintering the fibrous matrix at a temperature between 110° C. and 150°, wherein after sintering the PVDF-based polymer includes the beta form crystalline structure in an amount exceeding any other crystalline structure form in the crystalline PVDF phase.

11. The method of claim 10, further including coating the fibrous matrix with a material that increases the wettability of the fibrous matrix as compare to an uncoated fibrous matrix.

12. The method of claim 10, wherein the sintering is for a time ranging from 10 minutes to 20 minutes.

13. The method of claim 10, further including adding a solvent to the blend before electro-spinning.

14. The method of claim 10, further including adding a metal salt solution to the blend before electro-spinning.

15. The method of claim 10, wherein the crystalline PVDF phase further includes an alpha form crystalline structure and a ratio of the beta form to the alpha form is at least about 50 to 1.

16. The method of claim 10, wherein the additive includes a polymer that is miscible with the PVDF-based polymer.

17. The method of claim 10, wherein the additive includes at least one of polyacrylonitrile, poly(butyl methacrylate), polycaprolactone, poly(methyl methacrylate), polysulfone, and polyvinyl chloride.

18. The medical electrical lead of claim 17, wherein the additive includes poly(methyl methacrylate).

* * * * *